United States Patent [19]
Förster et al.

[11] Patent Number: 5,260,490
[45] Date of Patent: Nov. 9, 1993

[54] PROCESS FOR RECOVERING RHODIUM FROM THE REACTION PRODUCTS OF THE OXO SYNTHESIS

[75] Inventors: Ingrid Förster, Mülheim/Ruhr; Klaus Mathieu, Oberhausen, both of Fed. Rep. of Germany

[73] Assignee: Hoechst Aktiengesellschaft, Fed. Rep. of Germany

[21] Appl. No.: 960,897

[22] Filed: Oct. 14, 1992

[30] Foreign Application Priority Data

Oct. 24, 1991 [DE] Fed. Rep. of Germany ....... 4135049

[51] Int. Cl.$^5$ ................... C07C 45/50; C07C 45/78
[52] U.S. Cl. ........................... 568/454; 568/492
[58] Field of Search .............. 568/426, 449, 454, 492; 502/24, 26; 55/27

[56] References Cited

U.S. PATENT DOCUMENTS

| | | | |
|---|---|---|---|
| 4,731,485 | 3/1988 | Cornils et al. | 568/454 |
| 4,871,879 | 10/1989 | Laird | 568/454 |
| 5,091,350 | 2/1992 | Cornils et al. | 568/454 |
| 5,110,990 | 5/1992 | Blessing et al. | |

Primary Examiner—Werren B. Lone
Attorney, Agent, or Firm—Jordan B. Bierman

[57] ABSTRACT

A process for separating and recovering rhodium from oxo synthesis products comprising extracting under pressure an oxo synthesis product containing rhodium with an aqueous solution of a complexing organic phosphine to obtain a solution of a water-soluble phosphine substituted rhodium carbonyl compound.

14 Claims, 1 Drawing Sheet

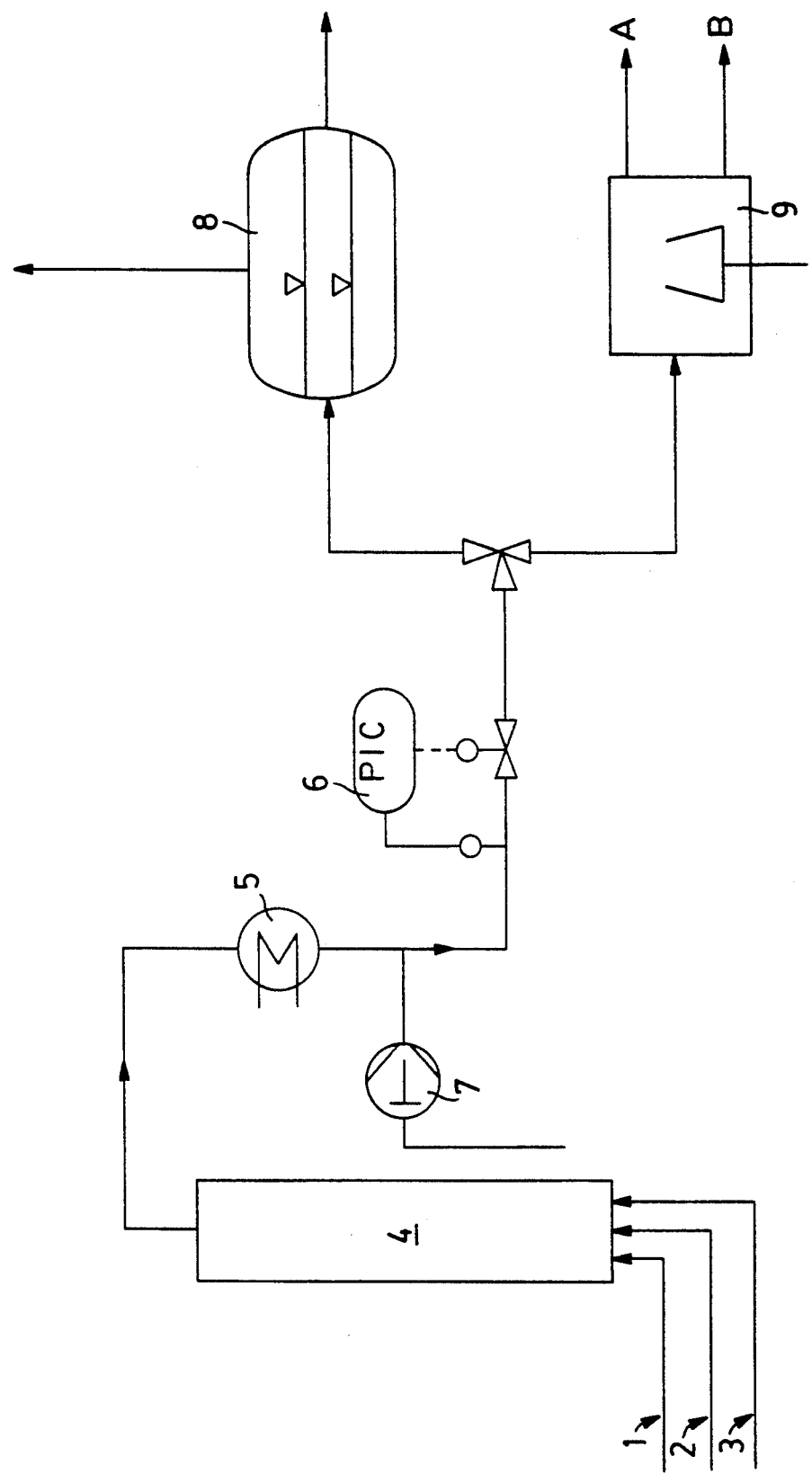

PROCESS FOR RECOVERING RHODIUM FROM THE REACTION PRODUCTS OF THE OXO SYNTHESIS

STATE OF THE ART

The preparation of aldehydes and alcohols by addition of carbon monoxide and hydrogen onto olefinic double bonds (hydroformylation) is known. The reaction is catalyzed by metals of Group VIII of the Periodic Table of the Elements, or compounds thereof, which form carbonyls or hydrocarbonyls under the reaction conditions. While previously cobalt and cobalt compounds were used almost exclusively as catalysts, rhodium catalysts are increasingly being used today, although rhodium is several times more expensive than cobalt. Rhodium is used by itself or in combination with complexing agents, for example organic phosphines or phosphites. While the oxo synthesis with rhodium as the catalyst requires reaction pressures of 25 to 30 MPa, pressures of 1 to 5 MPa are sufficient when rhodium is used in combination with complexing agents.

There are significant advantages for rhodium catalysts in many cases. They have a higher activity and selectivity, and moreover render problem-free operation of the production plant possible, particularly with respect to carrying out the synthesis and discharging the products from the reactor. Finally, the classical oxo process based on cobalt catalysts in many cases can be changed over to rhodium catalysts using the existing apparatus components with only small investments.

However, separating off and recovering the rhodium employed as the catalyst without complexing agents from the reaction product with exclusion of losses presents considerable difficulties. According to the prior art, the reaction product of the oxo synthesis is usually let down in at least two stages. To separate off dissolved synthesis gas, the pressure is first reduced from the synthesis pressure, i.e. about 25 to 30 MPa, to 1.5 to 2.5 MPa, and the pressure is then reduced to normal pressure, if appropriate via intermediate stages. Before purification of the crude reaction product, for example by distillation or its further processing to secondary products, the rhodium compounds dissolved homogeneously in the product which are present in a concentration of only a few ppm must be separated off. It must be remembered here that, during the letting down operation, rhodium is converted partly into the metallic form, or forms polynuclear carbonyls. In both cases, the result is the formation of a heterogeneous system which is made up of the liquid organic phase and the solid phase comprising rhodium or rhodium compounds.

In the process of DE-A1 3,347,406, the rhodium is separated off and recovered from the crude product, i.e. the reaction mixture obtained after letting down and, if appropriate, cooling, with the aid of complexing reagents under normal pressure. Sulfonates or carboxylates of organic phosphines which form water-soluble complex compounds with the rhodium are preferably employed as the complexing agents and the noble metal can therefore be extracted with aqueous solutions of the phosphines. During this operation, the rhodium passes into the aqueous phase which can be separated off from the organic product mixture by simple decantation. High rhodium concentrations can be achieved in the aqueous phase by circulating the solution of the complexing agent.

In order to accelerate and to bring to completion the extraction of the rhodium from the organic phase and its transfer into the aqueous phase, according to DE-A1 3,411,034, a solubilizing agent is added to the aqueous solution of the complexing agent. Its effect comprises above all changing the physical properties of the interfaces between the two liquid phases and in this way accelerates the transfer of the aqueous extraction agent into the product phase and of the rhodium from the product phase into the aqueous complexing agent phase. The extraction is simplified and the expenditure on apparatus is reduced by also using a solubilizing agent.

A further development of the above process is described in DE-A1 3,443,474 which uses tetraorganylammonium salts of sulfonated triarylphosphines which have both a complexing action and solubilizing properties for extraction of rhodium from the products of the oxo synthesis.

The known processes have proved themselves to be excellent in practice. In industrial operation, they enable up to about 95% of the rhodium originally employed to be separated off from the oxo reaction products and to be reusable. However, in view of the high price of the noble metal, there is interest in further improving the recovery of the rhodium.

OBJECTS OF THE INVENTION

It is an object of the invention to provide an improved process for the separation and recovery of rhodium from oxo synthesis products in a high yield.

This and other objects and advantages of the invention will become obvious from the following detailed description.

THE INVENTION

The novel process of the invention for separating and recovering rhodium from oxo synthesis products comprises extracting under pressure an oxo synthesis product containing rhodium with an aqueous solution of a complexing organic phosphine to obtain a solution of a water-soluble phosphine substituted rhodium carbonyl compound. Surprisingly, the proportion of rhodium recovered, based on the metal employed, can be further increased by the process of the invention as compared with the prior art.

An essential feature of the process is that the rhodium dissolved in the product of the oxo synthesis is extracted under increased pressure which prevents the catalytically active rhodium carbonyl compound from decomposing and in this way is withdrawn from immediate reaction with the water-soluble phosphine. According to the opinion predominantly held by experts, rhodium hydridocarbonyl is the catalytically active compound in hydroformylation catalyzed by rhodium (cf., for example, Greenwood, et al, Chemistry of the Elements, 1984, pages 1317-1319). When carrying out the process of the invention, pressure conditions under which rhodium hydridocarbonyl is capable of existence at the temperature chosen are therefore to be maintained in the reaction product after the synthesis. It has proved appropriate to maintain temperatures of between 0° and 200° C., preferably 20° to 130° C.

According to a specific embodiment of the invention, the extraction with the water-soluble organic phosphine is carried out under the conditions of the hydroformylation, i.e. in the presence of synthesis gas and at the synthesis temperature and pressure. This procedure contrasts with the known working-up processes in which the reaction product is first let down and degassed before the rhodium is separated off.

Water-soluble organic phosphines which are capable of complexing with rhodium are preferably compounds of the formula

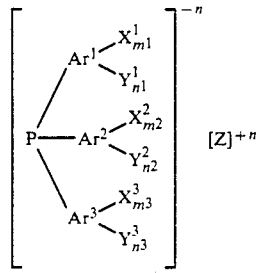

wherein $Ar^1$, $Ar^2$ and $Ar^3$ are individually benzene or naphthalene, $Y^1$, $Y^2$ and $Y^3$ are individually alkyl or alkoxy of 1 to 4 carbon atoms, halogen or —OH, —CN, —NO$_2$ or $R^1R^2N$—, $R^1$ and $R^2$ are individually alkyl of 1 to 4 carbon atoms, $X^1$, $X^2$ and $X^3$ are individually sulfonate (—SO$_3^-$) or carboxylate (—COO$^-$), $m^1$, $m^2$ and $m^3$ are individually integers from 0 to 3, and at least one of $m^1$, $m^2$ or $m^3$ is equal to or greater than 1, $n^1$, $n^2$ and $n^3$ are individually integers from 0 to 5, n is an integer from 1 to 9 and Z is alkali metal or ammonium ions or the equivalent of an alkaline earth metal or of zinc.

Particularly suitable extraction agents in the context of the procedure are phosphines of the formula above wherein $Ar^1$, $Ar^2$ and $Ar^3$ are benzene which is unsubstituted or substituted by a sulfonate, with the proviso that at least one benzene is substituted by a sulfonate, i.e. $X^1$, $X^2$ and/or $X^3$ are —SO$_3^-$, $m^1$, $m^2$ and $m^3$ are 0 or 1 and the sum of $m^1$, $m^2$ and $m^3$ is 1, 2 or 3, and furthermore $n^1$, $n^2$ and $n^3$ are each zero. Cations $Z^+$ of the water-soluble organic phosphines are preferably alkali metal ions, particularly sodium ions.

It is not necessary to use the water-soluble organic phosphines as uniform compounds. Mixtures of various phosphines can also be used in the process of the invention. Examples of phosphines which have proved to be particularly appropriate for extraction of rhodium are tri-Na-phenyltrisulfophenylphosphine (called TPPTS for short), di-Na-phenyldisulfophenylphosphine (called TPPDS for short) and mono-Na-diphenylsulfophenylphosphine (called TPPMS for short). The compounds are used individually or, preferably as a mixture.

To facilitate penetration of the aqueous (extraction) phase into the organic reaction product and in this way to increase the rate and completeness of the extraction, the extraction can be carried out in the presence of commercially available solubilizing agents (phase transfer reagents). Both anionic reagents such as lauric acid, myristic acid or stearic acid, and cationic reagents, i.e. amines such as octadecyldiethylamine and octadecylethanolamine, and neutral reagents such as adducts of ethylene oxide on higher molecular weight alcohols, on phenols and on fatty acids are suitable.

The complexing phosphines are used in a molar excess, based on the rhodium. Since they can be recirculated for renewed extraction, the level of the excess is not critical, but at least 5 moles of complexing phosphine should be present per mole of rhodium. It has proved to be particularly appropriate to use 60 to 100 moles, and with recycling even up to 500 moles of complexing phosphine per mole of rhodium.

The complexing phosphine is usually used in the form of a solution. It should be remembered here that, like the rhodium complex formed, it is largely insoluble in the reaction product while it is readily soluble in the solvent for the complexing reagent. The solvent should also be immiscible or only very slightly miscible with the reaction product.

When these conditions are met, a two-phase system which comprises the reaction product and the solution of the complexing phosphine and of the resulting rhodium complex compound is formed. The complexing agent acts as an extraction agent, i.e. in the initial state, the rhodium is dissolved in the reaction product, and in the final state, it is dissolved in the solution of the complexing agent.

The reaction product and the rhodium-containing solution are separated by the basic operations of chemical process technology which are customary for this process, for example by decantation or centrifugation. The preferred solvent for the complexing reagent and the rhodium complex is water but it is also possible to use mixtures of water with other solvents since lower alcohols such as methanol as long as it is ensured that the oxo reaction product and the solvent do not mix with one another and the solubility of the rhodium-phosphine complex in the aqueous phase is not impaired.

The concentration of the complexing reagent in the solution can be varied within wide limits depending on the extent to which the rhodium is to be enriched. Accordingly, not only saturated but even very dilute solutions can be employed. Solutions which contain 0.5 to 50% by weight and preferably 5 to 35% by weight (in each case based on the solution) of the complexing agent are as a rule used.

If the complexing agent is liquid under the extraction conditions and is insoluble or sparingly soluble in the hydroformylation product, and furthermore the rhodium complex is soluble in the complexing phosphine, it is also possible to dispense with the co-use of a solvent, i.e. the pure complexing agent can be employed. The process can be carried out either batchwise or continuously.

The further treatment or further use of the phase containing the rhodium separated off depends on the particular circumstances. The rhodium can thus be separated off in a known manner, for example by conversion into the salt of a higher carboxylic acid, and employed again as the catalyst. However, it is also possible for the phase comprising solvent, rhodium and complexing agent to be used directly as the catalyst system.

The process of the invention is suitable for separating off and recovering rhodium from the most diverse products of the oxo synthesis. It can be used successfully not only on crude products which are formed by hydroformylation of straight-chain or branched acyclic, olefinic hydrocarbons, particularly those having 2 to 20 carbon atoms but it has also proved to be excellent for separating off rhodium from products of hydroformylation of other olefinically unsaturated compounds, for example unsaturated alcohols, aldehydes and carboxylic acids, and furthermore diolefins and cyclic olefins such as dicyclopentadiene.

REFERRING NOW TO THE FIGURE

A technical embodiment of the operating procedure is shown in the attached FIGURE and the process of the invention can of course also be realized in other process variants.

Synthesis gas, olefin, and rhodium catalyst dissolved homogeneously in an organic phase are fed to a reactor 4 by lines 1, 2, and 3, respectively. The product which has been cooled in a heat exchanger 5 if appropriate is drawn off via a valve 6 with an adequate pressure to prevent decomposition of the rhodium hydrocarbonyl being maintained with synthesis gas. An aqueous phase containing the complexing agent is admixed to the product stream in a pipeline section via a pump 7. Intensive mixing of the phases and virtually complete extraction of the rhodium are achieved in this manner and the organic and aqueous phases are separated in separating vessel 8 or in centrifuge 9.

In the following examples, there are described several preferred embodiments to illustrate the invention. However, it is to be understood that the invention is not intended to be limited to the specific embodiments. All concentrations are expressed in percent by weight.

EXAMPLE 1

Dicyclopentadiene was hydroformylated in an autoclave equipped with a magnetic stirrer at 130° C. under a synthesis gas pressure ($CO:H_2 = 1:1$) of 27 MPa in the presence of 60 ppm by weight of rhodium (based on the dicyclopentadiene) as the catalyst. When the reaction had ended, the pressure was reduced to 25 MPa and an aqueous TPPTS solution was pumped in at 130° C. in an amount such that the P(III)/Rh molar ratio was 100:1. The mixture was stirred for about 2 to 3 minutes and was then transferred into a stirred flask with a bottom outlet, and heated at 60° C. with stirring. When the stirring had ended, separation of the phases started immediately, and was concluded after about 30 minutes. Analysis of the aqueous phase showed that 94 to 96% of the rhodium employed for the hydroformylation had been extracted. By subsequent washing of the organic phase, it was possible to increase the proportion of rhodium recovered to 97 to 98% (based on the amount of rhodium employed in the hydroformylation), corresponding to a rhodium residual concentration in the organic phase of 0.7 to 0.9% by weight. Alternatively, the phases can be separated by centrifugation at room temperature and in this case, subsequent washing is not necessary.

EXAMPLES 2 TO 4

Example 1 was repeated under changed pressure conditions. The reaction conditions and extraction results are summarized in the following table.

TABLE

| Temperature (°C.) | Pressure (MPa) | Rh recovery* |
|---|---|---|
| 80 | 27.0 | 98.6 |
| 80 | 5.0 | 97.0 |
| 130 | 5.0 | 97.8 |

*in %. based on the rhodium employed in the hydroformylation

Various modifications of the process of the invention may be made without departing from the spirit or scope thereof and it should be understood that the invention is intended to be limited only as defined in the appended claims.

What we claim is:

1. A process for separating and recovering rhodium from oxo synthesis products comprising extracting under pressure an oxo synthesis product containing rhodium with an aqueous solution of a complexing organic phosphine to obtain a solution of a water-soluble phosphine substituted rhodium carbonyl compound.

2. The process of claim 1 wherein the complexing organic phosphine has the formula

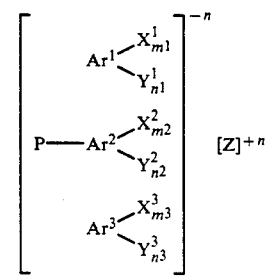

wherein $Ar^1$, $Ar^2$ and $Ar^3$ are individually benzene or naphthalene, $Y^1$, $Y^2$ and $Y^3$ are individually alkyl and alkoxy of 1 to 4 carbon atoms, halogen or —OH, —CN, —$NO_2$ or $R^1R^2N$—, $R^1$ and $R^2$ are individually alkyl of 1 to 4 carbon atoms, $X^1$, $X^2$ and $X^3$ are individually sulfonate (—$SO_3^-$) or carboxylate (—$COO^-$), $m^1$, $m^2$ and $m^3$ are individually integers from 0 to 3, and at least one of $m^1$, $m^2$ or $m^3$ is equal to or greater than 1, $n^1$, $n^2$ and $n^3$ are individually integers from 0 to 5, n is an integer from 1 to 9 and Z is alkali metal or ammonium ions or the equivalent of an alkaline earth metal or of zinc.

3. The process of claim 2 wherein $Ar^1$, $Ar^2$ and $Ar^3$ are benzene, $X^1$, $X^2$ and/or $X^3$ are sulfonate, the sum of $m^1$, $m^2$ and $m^3$ is 1 to 3 and $n^1$, $n^2$ and $n^3$ are each zero.

4. The process of claim 2 wherein the cation $Z^{+n}$ is an alkali metal ion.

5. The process of claim 4 wherein $Z^{+n}$ is a sodium ion.

6. The process of claim 1 wherein the extraction is effected at temperatures of between 0° and 200° C.

7. The process of claim 6 wherein the temperature is 20° to 130° C.

8. The process of claim 1 wherein the rhodium is extracted under the temperature and pressure conditions of the hydroformylation.

9. The process of claim 1 wherein at least 5 moles of water-soluble organic phosphine are used per mole of rhodium.

10. The process of claim 9 wherein 60 to 100 moles of phosphine are used per mole of rhodium.

11. The process of claim 1 wherein the concentration of the water-soluble organic phosphine in the aqueous solution is 0.5 to 50% by weight.

12. The process of claim 11 wherein the phosphine concentration is 5 to 35% by weight.

13. The process of claim 1 wherein the extraction of the rhodium is carried out in the presence of a solubilizing agent.

14. The process of claim 1 wherein a temperature at which said process is carried out and said pressure are such that said rhodium carbonyl compound is stable.

* * * * *